United States Patent [19]

Bolz

[11] 4,067,959

[45] Jan. 10, 1978

[54] INDIRECT SOLID SURFACE TEST FOR ANTIGENS OR ANTIBODIES

[75] Inventor: Gunner Bolz, Santa Clara, Calif.

[73] Assignee: International Diagnostic Technology, Inc., Santa Clara, Calif.

[21] Appl. No.: 684,775

[22] Filed: May 10, 1976

[51] Int. Cl.² ............... G01N 33/00; A61K 43/00
[52] U.S. Cl. ............................ 424/1; 23/230 B; 23/259; 424/12
[58] Field of Search .............. 424/1, 1.5, 12; 23/230 B, 259

[56] References Cited

U.S. PATENT DOCUMENTS

| | | | |
|---|---|---|---|
| 3,720,760 | 3/1973 | Bennich et al. | 424/1 |
| 3,896,217 | 7/1975 | Johnson | 424/1 |
| 3,940,475 | 2/1976 | Gross | 424/1 |

OTHER PUBLICATIONS

Crosignani et al., Journal of Clinical Endocrinology and Metabolism, vol. 30, No. 2, Feb., 1970, pp. 153–160.
Miles et al., Analytical Biochemistry, vol. 61, No. 1 Sept., 1974, pp. 209–224.
Catt, Acta Endocrinologica Supplementum, No. 142, 1969, pp. 222–246.

*Primary Examiner*—Benjamin R. Padgett
*Assistant Examiner*—Christine M. Nucker
*Attorney, Agent, or Firm*—Flehr, Hohbach, Test, Albritton & Herbert

[57] ABSTRACT

An indirect method for the quantitation of an antigen or antibody in a liquid sample. In the antigen assay, antigen of the same type as the sample antigen is adsorbed onto a solid support surface. Then, specific labelled antibody is immunologically reacted in solution with the sample antigen and the adsorbed antigen. The quantity of reacted labelled antibody on the solid support surface is then determined, as for example, fluorogen label by a fluorometer. The procedure is employed for detection of antibody by reversing the antigen and antibody components in each instance.

28 Claims, No Drawings

INDIRECT SOLID SURFACE TEST FOR ANTIGENS OR ANTIBODIES

BACKGROUND OF THE INVENTION

Various methods for solid-phase radioimmunoassay (RIA) of antigens or antibodies in a serum sample are known. In one technique, Catt and his co-workers have performed this technique on the interior surface of test tubes as set forth in U.S. Pat. No. 3,646,346. There, an excess of specified antibody is first adsorbed onto the tube wall. Then, the sample to be assayed is immunologically reacted with such surface as in a competitive binding technique. That is, the sample antigen to be determined and a known quantity of radioactively labelled antigen are simultaneously immunologically reacted with the antigen adsorbed on the tube wall. The labelled antigen reacted on the tube wall is then quantitated as an indication of the quantity of antigen in the original sample. The disadvantage of an RIA system in comparison to a fluorogenic one are well known and include inaccuracies due to the "noise" of the system at low signal levels, a limited shelf life of radioisotopes and the requirement of special licensing, handling and disposal of radioactive materials.

Another disadvantage of the Catt technique for mass production is the excessive tim (e.g., 2 to 24 hours) stated for adsorption. It is believed that this long time was necessary to completely coat the tube surface to prevent significant error due to nonspecific adsorption of labelled antibody.

There is a vague suggestion in the patent that the technique could be adpated for fluorometric readings. However, it would be extremely difficult to obtain an accurate fluorometric reading from he test tube interior surface because of the geometry of the tube and the interference from reading through the tube wall.

Another type of assay employing a radioactive label is disclosed in a book entitled *RIA Methods (Kirkham and Hunter, editors), Livingston, London,* 1971, 447–460. In this technique, designated the "immunoradiometric assay" the antigen to be detected is incubated in solution with an excess of labelled antibody. Then, solid phase particles covalently coupled to antigen are added to the solution and immunologically reacted with the excess free labelled antibody. Then, the solid phase particles are separated, and washed. Measurement of the radioactive label on the particles is an indirect indication of the antigen in solution. As set forth in Miles et al., *Nature, Lond.* 219, 186–189, this is generally a more sensitive and rapid technique than the competitive RIA technique as of the aforementioned Catt et al. type. One problem with the immunoradiometric technique described in Kirkham et al. is due to the specified immunoadsorbent surface substrates. That is, affinity purification is required, a time consuming procedure. This requirement is due to the difficulty of removing all traces of unreacted labelled antibody from the porous surfaces. Another problem is the tedious procedure required to measure the particulate surface. Other problems with this system derive from the use of a radioactive label.

SUMMARY OF THE INVENTION AND OBJECTS

In accordance with the present invention, a method is provided for quantitating antigen or antibody in a liquid sample performed on a solid surface. For simplicity of description, the material quantitated is assumed to be an immunoglobulin antigen in a sample of blood serum. Antigen of the same immunological type as the sample antigen is adsorbed directly onto a solid support surface, such as a polyacrylic polymer adsorptive to the antigen. Alternatively, the antigen may be ionically bonded as to an ion exchange resin. A known quantity of specific labelled antibody for the sample antigen is immunologically reacted with such antigen in solution and with the antigen previously adsorbed onto the surface. By employing an excess of labelled antibody, the amount of such antibody which reacts with the antigen adsorbed on the surface is an indirect indication of the amount of antigen in the sample. After removal of unreacted labelled antibody from the surface, the quantity of reacted labelled antibody is measured. If the substance in the sample is to be detected as an antibody rather than an antigen, the foregoing procedure is carried out with a reversal of the antigen and antibody reactants. Thus, antibody is adsorbed onto the surface and labelled antigen is reacted with the unknown antibody in the sample.

It is an object of the invention to provide a rapid, accurate method for the quantitation of antigen or antibody on a solid surface which overcomes the aforementioned disadvantages of prior art techniques.

It is a further object of the invention to provide a method of the foregoing type to provide rapid and sensitive assays of human immunogolobulin concentrations in blood serum.

It is a particular object of the invention to provide a determination of the foregoing type using fluorometric quantitation.

Further objects and features of the invention will be apparent from the following description of its preferred embodiments.

DETAILED DESCRIPTION OF THE PREFERRED EMBODIMENTS

The present invention relates to an "indirect method" for the quantitation on a solid support surface of antigen or antibody contained in a liquid sample. For simplicity of description, the liquid sample described herein comprises blood serum. Also, the substance to be quantitated in the blood serum will be referred to as antigen.

Briefly summarized, the present invention may be accomplished by the following sequence of steps. Antigen of the same immunological type as the serum antigen to be detected is sorbed, preferably adsorption, to an immunologically solid support surface adsorptive for the antigen. Then, a known quantity of specific labeled antibody is immunologically reacted in solution with both the sample antigen and the antigen adsorbed onto the support surface. Thereafter, unreacted labelled antibody is removed and the quantity of reacted labelled antibody is measured. This procedure will be referred to as the "indirect method."

A preferred technique of sorption is by physical adsorption onto the support surface. For example, the surface is immersed into a test tube of diluted human serum. This serum includes the same antigen as the antigen to be measured. The support surface is thoroughly mixed with the antigen, as with an automatic shaker, for approximately 20 minutes.

A suitable solid support surface is formed of a water-soluble polymeric material sorptive for the antigen. Known materials of this type include hydrocarbon polymers such as polystyrene, polyethylene, polypropylene, polybutylene, butyl rubber and other synthetic rubbers. Other suitable organic polymers include silastic rubber, polyesters, polyamides, cellulose and cellulosic derivatives, acrylates, methacrylates, and vinyl polymers such as vinyl chloride, and polyvinyl fluoride. Copolymers such as graft copolymers of polystyrene are also useful. In addition to the foregoing materials, the solid support surface may comprise silica gel, silicone wafers, glass, insoluble protein and metallic surfaces (e.g., tantalum coated glass).

A particularly effective form for the solid support surface is a disc, such as formed of polymethylmethacrylate film. After completion of the reactions described hereinafter, the technique of reading the labelled substance on the support surface may follow the detection technique set forth in application Ser. No. 627,941, filed Nov. 3, 1975, entitled "Diagnostic Reagent Holder and Method."

After adsorption of the antigen (herein the "adsorption step"), the surface is washed with an appropriate solution to remove unadsorbed antigen and other components from the surface.

In another step, the antigen to be quantitated in the serum is mixed with an excess of a labelled specific antibody immunologically reactive with the antigen to cause an immunological reaction to occur in the solution. This step will be referred to as the "solution immunological reaction." This step is of sufficient duration for completion of the reaction, typically 1 minute to 2 hours. At completion of incubation, the labelled antibody in excess of antigen in solution is free to react with additional antigen.

After the solution immunological reaction, the support surface containing adsorbed antigen is immersed and mixed with the solution until the immunological reaction between the excess labelled antibody and antigen on the support surface proceeds essentially to completion. This step is referred to as the "solid surface immunological reaction." A suitable duration for this reaction is on the order of 5 minutes to 2 hours, during which the sample is constantly mixed as by shaking.

The labelled antibody which immunologically reacts with the antigen adsorbed surface is inversely related to the concentration of the antigen to be measured in the serum sample. This is because only free antibody which is not bound to the antigen in the serum is capable of reacting with the antigen on the support surface. In other words, the reacted antibody on the support surface is a measure of such unbound antibody.

After completion of the solid surface immunological reaction, the support surface is washed, as in a buffer wash solution, to remove unreacted labelled antibody from the surface which could interfere with quantitation. An effective washing solution comprises phosphate buffered saline solution.

After washing, the surface is read in an appropriate reading device. The present system is particularly adapted or fluorescent detection of the surface of a diagnostic reagent holder of the type set forth in the aforementioned reagent holder of the type set forth in the aforementioned co-pending patent application. Thus, the holder containing the fluorescently labelled disc is placed into a viewing housing for reading by a fluorometer. Such readings may be taken in less than 10 seconds.

The aforementioned fluorometric readings are compared against known reference preparations adsorbed similarly upon identical surfaces. For example, for the specific immunoglobulin to be read, calibration curves are prepared for different concentrations of immunoglobulin versus the fluorescent signal in arbitrary units. As guidance, the assay ranges for routine assay of human serum samples are as follows: IgG — 300 to 2,000 mg/dl; IgA — 35 to 330 mg/dl; and IgM — 15 to 300 mg/dl.

Suitable fluorescent labels include lissamine-rhodamine B, D.A.N.S. (1-dimethylamino-naphthalene-5-sulfonic acid), ortho-phthaladehyde, fluorescein isothiocyanate and fluorescamine, which are frequently used in fluorescence microscopy. The first two possess an orange or red emission spectra rather than the yellow fluorescein and the second two possess a blue or green emission spectra. The only variation in the fluorometer would be the change in exciation and emission filters used, as well as the changes in the fluorescent tag on the antibodies in the reagent kit.

When the label comprises a radioactive substance, a suitable reading device is a scintillation counter.

The present technique is also applicable to the use of enzyme labelled systems. One such system is described in an article by Pesce et al entitled "Use of Enzyme-linked Antibodies to Measure Serum Anti-DNA Antibody in Systemic Lupus Erthyematosus," Clin. Chem. 20/3, 353–359 (1974). The described system differs from the one described herein in that the diagnostic reagent, DNA, is adsorbed to a test tube support. Thereafter, anti-DNA antibody containing serum is reacted with the coated tube followed by reaction with an anti-human gamma globulin peroxidase enzyme conjugate. Then a colored reaction product is developed by action of peroxidase on a substrate which is colorimetrically measured by conventional techniques.

The present solid surface technique is preferably performed with a fluorescently labelled antigen or antibody. An effective reagent is a fluorescein isothiocyanate labelled monospecific antibody to human IgG, IgA or IgM in a buffered saline solution. Fluorescent labelling permits quantitation using a fluorometer reading a precise predetermined area comprising only the reaction support surface. This can be accomplished by viewing such surface through a window of a viewing housing framed by opaque material which permits detection of fluorescence emitted only from the surface. This would be difficult to accomplish with a radioactively labelled substance. A particularly effective viewing housing and reaction support surface is illustrated in the aforementioned patent application Ser. No. 627,941, incorporated herein by reference. The support surface comprises the disc attached to the diagnostic reagent holder of said application. The importance of viewing only the support surface is that there is a degree of carryover of labelled substance which attaches to the holder in addition to that which attaches to the disc. This is a particular problem in the present technique in which the sample protein may adsorb relatively nonspecifically in significant quantities to the holder as well as the disc, especially if the holder is formed of a polymer adsorptive for protein.

Although physical adsorption is preferred as the sorption technique employed herein because of its simplicity and the inexpensive nature of the support surface, it should be understood that other sorption techniques may be employed within the scope of the present invention. For example, specially treated ion exchange resins may be employed as the surface for ionic bonding of the antigen or antibody to be measured. This may be desirable for vitamin $B_{12}$ and other molecules that bind readily to ion exchange resins.

In the foregoing description, the solution immunological reaction proceeds to equilibrium prior to the solid surface immunological reaction. It has been found that when these reactions are carried out simultaneously only a slight shift in the assay range will result. Accordingly, these two steps may be performed either simultaneously or sequentially. It is believed that this interchangeability is based upon the extremely rapid immunological reaction rate in solution in comparison to the immunological reaction rate on the solid surface. Thus, the reaction proceeds essentially to completion in solution even in the presence of the antigen on the surface. Thus, the present indirect method is not a competitive technique.

A significant feature of the present indirect method is that it may be performed in a continuous test sequence for a predetermined antigen. A laboratory technician may choose from a wide variety of types and concentrations of antigens to be adsorbed onto the support surface. By selection of the concentration of antigen on the surface, the technician may control the dynamic range of the assay to correspond to the concentration of antigen expected in the serum.

The solid surface immunological reaction step preferably is performed prior to drying of the antigen adsorbed onto the support surface. In this manner, denaturation of the protein which may accompany drying is prevented. Thus, adsorption and washing is performed at a time significantly less than one hour prior to immunological reaction.

As set forth above, it has been found that the duration of the adsorption step may be reduced to a time significantly less than one hour, to as short as 1 to 30 minutes. This is to be contrasted with the long duration of adsorption to completion of Catt et al., who were likely concerned with interference from nonspecific adsorption of labelled antibody in the competitive step if there are significant areas of uncoated surfaces.

One reason for applicant's ability to shorten the time for the adsorption step is that this step need not proceed to completion in the present indirect technique. This is due to the use of a vast excess of protein buffer in the labelled antibody solution. Nonspecific adsorption during the solid immunological reaction would be dominated by the protein buffer compared to the labelled antibody. In other words, the amount of nonspecific adsorption of labelled antibody is negligible. Therefore, the adsorption step in the present method need not proceed to completion and so may be performed rapidly.

The prior art technique set forth in the book entitled "RIA Methods" utilizes covalent bonding of the particles designated immunoadsorbent. In contrast, the present solid support surface comprises a surface portion of a reagent holder with a suitable handle for mixing. Such surface portion is essentially flat (nonspherical) although some concavity or convexity may be tolerated. The surface is defined by a cross-sectional area of at least from 1 to 30 sq. mm. Also, the antigen is physically adsorbed to the support surface, a simple, rapid, precise procedure for a technician.

The foregoing description refers to determination of the concentration of serum antigen. For the determination of serum sample antibody, the procedure is employed with appropriate modifications. That is, antibody of the same type as the serum antibody is first adsorbed onto the support surface. Also, labelled antigen is reacted with the serum sample antibody in the solution immunological reaction.

A further disclosure of the nature of the present invention is provided by the following specific examples of the practice of the invention. It should be understood that the data disclosed serve only as examples and are not intended to limit the scope of the invention.

EXAMPLE 1

In the determination of the concentration of human IgG, the adsorption step is accomplished by using a solid support surface comprising a polymethylmethacrylate disc attached to a holder. The surface is coated with IgG by immersing the surface in an appropriate dilution of serum containing IgG and shaken for about 20 minutes to permit adsorption to occur. Thereafter, the surface is washed to remove unadsorbed immunoglobulin from the surface as with a protein buffer solution in another test tube.

The solution immunological reaction is then performed. Then, 0.005 ml of an appropriate dilution of the serum sample is mixed with 0.5 ml of an appropriate dilution of labelled antibody comprising monospecific FITC-labelled goat antibody to human IgG. Then the solution in the tube is thoroughly mixed by shaking to incubate the antigen and labelled antibody for about 25 minutes. Then, the support is grasped by the holder and immersed in the test tube containing IgG and labelled antibody. During this second stage of incubation, the support surface is thoroughly mixed by shaking the tube for approximately 10 to 30 minutes. Thereafter, the surface is again washed, as in a buffer solution comprising a phosphate buffer saline at a pH of 7.7 ± 0.1 including 0.1% sodium azide preservative, by shaking for 25 minutes. Then, the surface is read with a fluorometer.

The fluorescence of the sample is compared against reference samples containing known quantities of antigen, i.e., the immunoglobulin to be quantitated. The base references are prepared from pooled human serum standardized by reference to WHO immunoglublin reference preparations. Suitable concentrations to perform a calibration curve may be found from the following chart:

| Calibrator | Typical Concentration for Three Calibration Samples | | |
|---|---|---|---|
| | IgG | IgA | IgM |
| Low | 50 mg/dl (6.22 IU/ml) | 50 mg/dl (35.2 IU/ml) | 25 mg/dl (29.5 IU/ml) |
| Medium | 130 mg/dl (16.2 IU/ml) | 200 mg/dl (141 IU/ml) | 150 mg/dl (177 IU/ml) |
| High | 200 mg/dl (24.9 IU/ml) | 300 mg/dl (211 IU/ml) | 200 mg/dl (354 IU/ml) |

EXAMPLE 2

The technique of the preceding example is followed with the exception that the time between the commencement of the solution immunological reaction and immersion of the surface for the solid surface immunological reaction is reduced to less than 3 minutes. Thus, the reactions are performed almost simultaneously. The only difference is result of any significance is that the calibration curve illustrates a slight shift (less than 10%) in the effective assay range.

What is claimed is:

1. In an indirect method for the quantitation of antigen in a liquid sample, the steps of
   a. sorbing antigen of the same immunological type as said sample antigen onto a sorptive solid support surface,
   b. immunologically reacting a known quantity of specific labelled antibody in solution with said sample antigen in said solution and with said sorbed antigen, said labelled antibody being in excess of said sample antigen, so that a portion of said labelled antibody is bound in said solution to said sample antigen and excess labelled antibody immunologically reacts with the sorbed antigen on said surface,
   c. washing said surface, and
   d. measuring the quantity of reacted labelled antibody on said surface.

2. The method of claim 1 in which step (a) is performed by physical adsorption of said antigen to said support surface.

3. The method of claim 2 in which step (a) is performed at a time no greater than about 1 hour prior to step (b).

4. The method of claim 2 in which step (b) is performed without drying of the antigen sorbed in step (a).

5. The method of claim 2 in which prior to step (b) said labelled antibody is mixed with excess protein buffer immunologically unreactive with said labelled antibody.

6. The method of claim 1 in which the labelled portion of said labelled antibody is selected from the group consisting of a luminescent substance, a radioactive substance, an enzyme or metal containing substance.

7. The method of claim 1 in which the labelled portion of said labelled antibody comprises a fluorogen, and said measurement step (d) is accomplished by fluorometric reading.

8. The method of claim 1 in which the reaction of step (b) is performed by first incubating sai labelled antibody and sample antigen in solution and thereaftr exposing said sorbed surface to the incubated reaction product for reaction of remaining unreacted labelled antibody in the solution with said support surface.

9. The method of claim 1 in which the reaction of step (b) is performd by simultaneous contact of said antigen-sorbed support surface with said labelled antibody and sample antigen in solution without prior incubation.

10. The method of claim 1 in which said support surface comprises a surface portion of a reagent holder.

11. The method of claim 8 in which said surface portion is nonspherical with a cross-sectional area of at least 1 sq. mm.

12. In an indirect method for the quantitation of antibody in a liquid sample, the steps of
   a. sorbing antibody of the same immunological type as said sample antibody to a sorptive solid support surface,
   b. immunologically reacting a known quantity of specific labelled antigen in solution with said sample antibody and with said sorbed antibody, said labelled antigen being in excess of said sample antibody so that a portion of said labelled antigen is bound to said sample antibody in solution and excess labelled antigen immunologically reacts with the sorbed antibody on said surface,
   c. washing said surface, and
   d. measuring the quantity of reacted labelled antigen on said surface.

13. The method of claim 12 in which step (a) is performed by physical adsorption of said antibody.

14. The method of claim 13 in which step (a) is performed at a time no greater than about 1 hour prior to step (b).

15. The method of claim 13 in which step (b) is performed without drying of the antibody sorbed in step (a).

16. The method of claim 13 in which prior to step (b) said labelled antigen is mixed with excess protein buffer immunologically unreactive with said labelled antigen.

17. The method of claim 12 in which the labelled portion of said labelled antigen is selected from the group consisting of a luminescent substance, a radioactive substance, an enzyme or metal containing substance.

18. The method of claim 12 in which the labelled portion of said labelled antigen comprises a fluorogen, and said measurement step (d) is accomplished by fluorometric reading.

19. The method of claim 12 in which the reaction of step (b) is performed by first incubating said labelled antigen and sample antibody in solution and thereafter exposing said second sorbed surface to the incubated reaction product for reaction of remaining unreacted labelled antigen in the solution with said support surface.

20. The method of claim 12 in which the reaction of step (b) is performed by simultaneous contact of said antibody-sorbed support surface with said labelled antigen and sample antibody in solution without prior incubation.

21. The method of claim 12 in which said support surface comprises a surface portion of a reagent holder.

22. The method of claim 19 in which said surface portion is nonspherical with a cross-sectional area of at least 1 sq. mm.

23. An immunological system for the quantitation of antigen in a liquid sample comprising:
   a. a contained liquid volume including one quantity of labelled antibody immunlogically bound to sample antigen dispersed in said liquid volume, and
   b. antigen of the same immunological type as said sample antigen sobed directly to a solid support surface disposed in said liquid volume, said sorbed antigen being directly immunologically bound to another quantity of said labelled antibody.

24. The immunological system of claim 23 in which the labelled portion of said labelled antibody is selected from the group consisting of a luminescent substance, a radioactive substance, an enzyme or metal containing substance.

25. The immunological system of claim 23 in which said support surface comprises a support portion of a reagent holder.

26. An immunological system for the quantitation of antibody in a liquid sample comprising:
   a. a contained liquid volume including one quantity of labelled antigen immunologically bound to sample antibody dispersed in said liquid volume, and
   b. antibody of the same immunological type as said sample antibody sorbed directly to a solid support surface disposed in said liquid volume, said sorbed antibody being directly immunologically bound to another quantity of said labelled antigen.

27. The immunological system of claim 26 in which the labelled portion of said labelled antigen is selected from the group consisting of a luminescent substance, a radioactive substance, an enzyme or metal containing substance.

28. The immunological system of claim 26 in which said support surface comprises a support portion of a reagent holder.

* * * * *